United States Patent [19]

Cooper et al.

[11] Patent Number: 4,587,053

[45] Date of Patent: May 6, 1986

[54] PREPARATION OF OXAZOLINES

[75] Inventors: Robin D. G. Cooper; John M. Morin, Jr., both of Indianapolis, Ind.; Lynn R. Peters, Defiance, Ohio

[73] Assignee: Eli Lilly and Company, Indianapolis, Ind.

[21] Appl. No.: 604,282

[22] Filed: Apr. 26, 1984

[51] Int. Cl.[4] .......... C07D 498/04

[52] U.S. Cl. .......... 260/245.4

[58] Field of Search .......... 260/245.4

[56] References Cited

U.S. PATENT DOCUMENTS 4,220,766 9/1980 Tsuji et al. .......... 544/182

OTHER PUBLICATIONS

Yanagisawa et al., Tetrahedron Letters, vol. 23, No. 33, pp. 3379-3382, (1982).

*Primary Examiner*—Mark L. Berch

*Attorney, Agent, or Firm*—Charles W. Ashbrook; Arthur R. Whale

[57] ABSTRACT

Oxazolino-azetidinones are prepared by reaction of a phosphorus compound with a 3-exomethylenecepham sulfoxide.

10 Claims, No Drawings

PREPARATION OF OXAZOLINES

BACKGROUND OF THE INVENTION

The cephalosporin group of antibiotics has found widespread success in the treatment of bacterial infections. Cephalosporins generally have a much broader spectrum of activity than the penicillins, and have routinely been employed in situations where penicillin therapy is not indicated. More recently, a group of compounds that appears even more active antibacterially than the cephalosporins has been discovered. This new class of compounds is characterized as the 1-oxadethiacephalosporins.

While these compounds are in many respects superior to the cephalosporins, their widespread clinical use has been hindered by their high cost due to their difficulty of manufacture. For example, U.S. Pat. No. 4,220,766 describes a multi-step synthesis of certain 1-oxadethiacephalosporins starting from certain penicillin sulfoxides. Another multi-step synthesis is reported in U.S. Pat. No. 4,323,567.

Tsuji et al., in U.S. Pat. No. 4,220,766, found that a very useful intermediate in the synthesis of certain 1-oxadethiacephalosporins is an oxazoline derivative, namely an oxazoline bearing an allylic alcohol grouping. The reference teaches that such compounds can be cyclized in one step to a 1-oxadethiacephalosporin. However, the synthesis of the oxazoline involved numerous complicated steps. For example, the use of 3-exomethylene cephalosporin sulfoxides as starting materials in the synthesis of oxazolines is reported by Yanagisawa in *Tetrahedron Letters,* 23, pp. 3379–3382 (1982). That process involves the conversion of the cephalosporin sulfoxide to a heterocyclic disulfide derivative, which is subsequently converted to an oxazoline.

An object of this invention is to provide a one-step conversion of a 3-exomethylene cephalosporin sulfoxide to an oxazoline that bears an allylic alcohol substituent.

SUMMARY OF THE INVENTION

This invention concerns a chemical process for converting 3-exomethylene cephalosporin sulfoxides to oxazolino-azetidinone compounds. The invention provides a process for preparing a compound of the formula

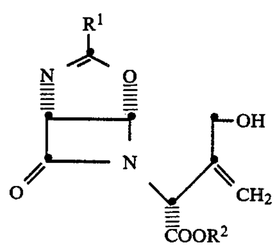

which comprises reacting a tri-substituted phosphorus compound with a 3-exomethylene cepham sulfoxide of the formula

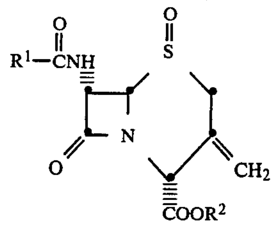

wherein:

$R^1$ is a monovalent residue of a carboxylic acid less the carbonyl group; and $R^2$ is a carboxy protecting group.

DETAILED DESCRIPTION OF THE INVENTION

The process provided by this invention can be carried out on any 3-exomethylenecepham sulfoxide that is stable to the reaction conditions. For example, 3-exomethylenecepham sulfoxides having a variety of possible side chains are well known in the art and can be employed as substrates in the present process. All that is required of the cepham substrate is that it bear an amido group

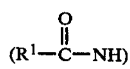

in the 7α position. As used herein, $R^1$ defines a monovalent residue of a carboxylic acid, less the carbonyl group. Such $R^1$ group includes hydrogen; $C_1$–$C_6$ alkyl such as methyl, ethyl, isopropyl, isobutyl, tert.-butyl, cyclopentylmethyl; $C_7$–$C_{15}$ arylalkyl such as benzyl, phenethyl, diphenylmethyl; $C_7$–$C_9$ aryloxyalkyl such as phenoxymethyl, phenoxyethyl, phenoxypropyl; $C_6$–$C_{10}$ aryl such as phenyl, naphthyl; $C_1$–$C_6$ alkoxy such as methoxy, ethoxy, cyclopropylmethoxy, cyclohexyloxy; $C_7$–$C_{15}$ arylalkoxy such as benzyloxy, phenethyloxy; $C_6$–$C_{10}$ aryloxy such as phenoxy or naphthyloxy; carbamoyl; $C_2$–$C_7$ carbalkoxy. These groups can themselves be unsubstituted or substituted with another group such as hydroxy, $C_1$–$C_6$ alkanoyloxy, $C_1$–$C_3$ alkoxy, oxo, amino, $C_1$–$C_3$ alkylamino, $C_1$–$C_6$ acylamino, nitro, $C_1$–$C_3$ alkyl, $C_6$–$C_{10}$ aryl, carboxy, protected carboxy, cyano, halo, or similar such substituent groups. The aryl part of any of the foregoing groups containing aryl can be a five or six membered carbocyclic or heterocyclic aromatic group including phenyl, naphthyl, furyl, thienyl, pyrrolyl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, pyridyl, pyrimidyl, pyrazinyl, pyridazinyl, triazinyl, quinolyl, isoquinolinyl, benzothiazolyl, benzothienyl and indolyl.

Specific examples of $R^1$ include hydrogen, methyl, n-butyl, methoxymethyl, carbethoxy, trichloroethoxy, acetoxymethyl, chloroethyl, allyl, benzyl, nitrobenzyl, chlorobenzyl, aminobenzyl, acetamidobenzyl, bromobenzyl, methoxybenzyl, methylenedioxybenzyl, trimethoxybenzyl, dichlorobenzyl, hydroxybenzyl, phenethyl, chlorophenethyl, methylphenethyl, nitrophenethyl, methoxyphenethyl, diphenylmethyl, α-chlorobenzyl, α-bromobenzyl, benzyloxybenzyl, anisyloxybenzyl, α-protected carboxybenzyl, α-protected carboxy-p-anisyloxybenzyl, α-protected carboxy-p- diphenylmethoxybenzyl, α-protected carboxy-p-acetyloxybenzyl, furylmethyl, thienylmethyl, oxazolylmethyl, isoxazolylmethyl, thiazolylmethyl, thiadiazolylmethyl, pyrazolylmethyl, tetrazolylmethyl, α-carbalkoxy-α-thienylmethyl, carbomethoxy, carbethoxy, benzyloxycarbonyl, carbamoyl, phenoxymethyl, phenoxyethyl, phenoxypropyl, phenoxybutyl, isoxazolyloxymethyl, phenyl, tolyl, xylyl, hydroxyphenyl, acetoxyphenyl, methoxyphenyl, tert.-butyloxyphenyl, nitrophenyl, cyanophenyl, carbethoxyphenyl, aminophenyl, acetamidophenyl, methylaminophenyl, chlorophenyl, thienyl, furyl, pyrrolyl, oxazolyl, oxadiazolyl, oxatriazolyl, thiazolyl, thiadiazolyl, pyrazolyl, triazolyl, tetrazolyl, pyridyl, tert.-butoxy, cyclopropylmethoxy, cyclopropylethoxy, methanesulfonylethoxy, phenacyloxy, benzyloxy, xylyloxy, diphenylmethoxy, phenoxy, tolyloxy, naphthyloxy, pentachlorophenoxy, nitrobenzyloxy, pyridyloxy, benzothienyloxy, indolyloxy, and related groups.

The nature of the side chain portion of the 3-exomethylenecepham substrate is not critical to the process, and any specific side chain $$R^1C(=O)-$$

can be removed by standard side chain cleavage reactions, or introduced by normal acylation of a 7α-amino-3-exomethylenecepham. The specific side chain to be employed can be selected in consideration of stability during the process and subsequent use to be made of the product.

The term $R^2$ defines a carboxy protecting group, many of which are well known and routinely used in the cephalosporin art. The carboxy protecting group is simply an organic radical that serves to improve solubility characteristics of the parent 3-exomethylenecepham 4-carboxylic acid, and which aids in inhibiting unwanted side reactions that might otherwise occur during the course of the process. For example, a typical side reaction that may occur to some extent is lactonization of the oxazoline produced by the present process to give a compound of the formula

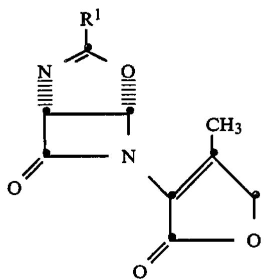

A preferred carboxy protecting group is one that is effective in minimizing such lactonization.

Typical carboxy protecting groups are ester forming groups having up to about 20 carbon atoms. For example, lower alkyl groups such as $C_1$–$C_5$ alkyl, including methyl, ethyl, tert.-butyl, cyclopropylmethyl, and the like can be employed. Other suitable carboxy protecting groups include $C_7$–$C_{20}$ arylalkyl groups such as diphenylmethyl, triphenylmethyl, 2-phenylethyl; $C_6$–$C_{10}$ aryl such as phenyl, indanyl, naphthyl; $C_3$–$C_{10}$ organometallic such as trimethylsilyl, ethoxydimethylsilyl, or trimethylstannyl.

$R^2$ may bear one or more substituent groups such as halo, hydroxy, $C_1$–$C_5$ alkanoyloxy, oxo, $C_1$–$C_5$ alkanoylamino, nitro, $C_1$–$C_5$ alkyl, carboxy, $C_2$–$C_6$ carbalkoxy, $C_1$–$C_5$ alkanoyl, or cyano. The aryl portions of any $R^2$ group can of course be heteroaromatic.

Examples of carboxy protecting groups commonly employed include methyl, ethyl, isopropyl, tert.-butyl, cyclobutylmethyl, chloromethyl, iodomethyl, 2,2,2-trichloroethyl, cyanomethyl, acetylmethyl, diacetylmethyl, allyl, acetoxymethyl, propionyloxymethyl, benzoyloxymethyl, methoxymethyl, methoxyethoxymethyl, phenoxymethyl, methylthiomethyl, phenylthiomethyl, tetrahydropyranyl, phthalimidomethyl, α,α-dimethylpropargyl, ethoxycarbonyloxyethyl, benzyl, phenethyl, tolylmethyl, dimethylbenzyl, phthalidyl, 4-hydroxy-3,5-di-tert-butylbenzyl, diphenylmethyl, methoxydiphenylmethyl, trityl, phenacyl, chlorophenacyl, bromophenacyl, phenyl, naphthyl, tolyl dimethylphenyl, nitrophenyl, methanesulfonylphenyl, chlorophenyl, pentachlorophenyl, indanyl, pyridyl and the like. Other typical carboxy protecting groups are described by Greene in *Protective Groups in Organic Synthesis,* John Wiley and Sons, N.Y., 1981, Chapter 5, and by Haslan in *Protective Groups in Organic Chemistry,* J. F. W. McOmie, Ed., Plenum Press, N.Y. 1973 Chapter 5.

The process provided by this invention is carried out by combining approximately equimolar quantities of a 3-exomethylenecepham sulfoxide with a trisubstituted phosphorus compound. The particular trisubstituted phosphine employed is not critical to the process; all that is required is that the phosphorus atom be trivalent. Typical trisubstituted phosphines that can be employed include triaryl phosphines such as triphenylphosphine, tri(methoxyphenyl)phosphine, tri(chlorophenyl)phosphine, tri(tolyl)phosphine, trinaphthylphosphine, trithienylphosphine; trialkylphosphines such as trimethylphosphine, tricyanoethylphosphine, tri-n-butylphosphine, tri-isopentylphosphine, tricyclohexylphosphine, and ethyl-dicyclopropylphosphine.

The process of the invention generally is carried out in an unreactive organic solvent. While the particular choice of solvent is not critical, a particularly preferred solvent is an organic dialkyl ketone, for instance acetone, methyl ethyl ketone, diethyl ketone, diisopropyl ketone, methyl n-butyl ketone and the like. Other solvents that can be routinely employed include aromatics such as benzene, toluene, xylene, chlorobenzene; ethers such as diethyl ether, methyl ethyl ether, diglyme, dioxane, tetrahydrofuran, methyl phenyl ether; esters such as ethyl acetate, isopropyl acetate, n-butyl acetate, methyl benzoate; alcohols such as ethanol, isopropyl alcohol, isobutyl alcohol, tert.-butyl alcohol, and related unreactive organic solvents.

The reaction generally is conducted at an elevated temperature of about 50° to about 100° C., and routinely is carried out at the reflux temperature of the reaction medium. The process normally is substantially complete after about thirty minutes to about four hours, although longer reaction periods do not appear detrimental to formation of the oxazoline product and can be employed if desired. The progress of the reaction can be followed by standard techniques such as thin layer chromatographic analysis, and upon substantially complete formation of the desired oxazoline, the reaction can be stopped by simply cooling the reaction mixture, for instance to a temperature of about 0° to 30° C.

The oxazoline that is produced by the present process can be readily isolated if desired by standard means. For example, following addition of a base such as aqueous sodium bicarbonate or the like, the reaction mixture can be filtered in order to remove any insoluble phosphorus sulfide derivative that is formed as a byproduct, and then the solvent can be removed from the filtrate, for instance by evaporation under reduced pressure. The product thus formed, an oxazoline of the above formula, can be purified further if desired by standard methods such as chromatography, crystallization or the like.

The oxazolines produced by the method of this invention are not new compounds, having been described in detail in U.S. Pat. No. 4,220,766. As pointed out in that reference, the oxazolines are useful since they are readily converted to 3-exomethylene-1-oxadethiacephams by reaction with an agent such as boron trifluoride. If desired, such conversion can be carried out in situ without isolating the oxazoline produced by the present process. For example, the process of this invention can be stopped at the appropriate time by addition of an aqueous base, and the organic layer can be separated and dried. Boron trifluoride can then be added directly to the organic layer so as to convert the oxazoline to the corresponding 3-exomethylene-1-oxadethiacepham.

The process of this invention is further illustrated by the following working examples.

EXAMPLE 1

Diphenylmethyl 7α-phenoxyacetamido-3-exomethylene-1-oxadethiacepham-4-carboxylate A solution of 200 mg (θ.37 mM) of diphenylmethyl 7α-phenoxyacetamido-1-oxo-3-exomethylenecepham-4-carboxylate and 100 mg (0.38 mM) of triphenylphosphine in 4 ml of methyl ethyl ketone was heated at reflux for ninety minutes. After cooling the reaction mixture to about 30° C., the solvent was removed by evaporation under reduced pressure to give an oil. The oil was dissolved in 2 ml of ethyl acetate and the mixture was filtered to remove undissolved triphenylphosphine sulfide. The filtrate was concentrated to dryness to give diphenylmethyl [2R-2-(3-phenoxymethyl-7-oxo-4-oxa-2,6-diazabicyclo[3.2.0]hept-2-en-6-yl]-3-hydroxymethyl-3-butenoate.

The product thus produced was dissolved in 2 ml of fresh ethyl acetate, to which was added 5λ (0.037 mM) of a 50% solution of boron trifluoride diethyl etherate in diethyl ether. The reaction mixture was stirred for about two hours, and then was diluted by addition of 0.8 ml of 0.5% (wt/v) aqueous sodium bicarbonate. The pH of the solution was adjusted to 6.8 by addition of 5% sodium bicarbonate. The reaction mixture was filtered and the organic layer was separated out of the filtrate. Removal of the solvent afforded 270 mg of a white foam. The foam was chromatographed on a 20×20×2 mm silica coated plate, eluting with a solution of 3 parts toluene and 2 parts ethyl acetate. The major band was removed and washed with acetonitrile. Removal of the solvent by evaporation afforded 50 mg of diphenylmethyl 7α-phenoxyacetamido-3-exomethylene-1-oxadethiacepham-4-carboxylate.

NMR: ($CDCl_3$) δ4.12 (s, 2H); δ, 4.45 (s, 2H), δ4.85 (d, 1H); δ5.2 (m, 3H); δ6.8–7.5 (m, 16H).

IR ($CHCl_3$) 1772 $cm^{-1}$, 1740 $cm^{-1}$, 1690 $cm^{-1}$, consistent with that of authentic sample.

Analysis calculated for $C_{29}H_{26}N_2O_6$: Theory: C, 69.87; H, 5.26; N, 5.62. Found: C, 69.65; H, 5.09; N, 5.41.

EXAMPLE 2

Diphenylmethyl [2R-2-(3-phenoxymethyl)-7-oxo-4-oxa-2,6-diazabicyclo[3.2.0]hept-2-en-6-yl]-3-hydroxymethyl-3-butenoate A solution of 200 mg (0.37 mM) of diphenylmethyl 7-α-phenoxyacetamido-1-oxo-3-exomethylenecepham-4-carboxylate in 4 ml of benzene containing 100 mg (0.38 mM) of triphenylphosphine was heated at reflux for seventy-five minutes. The reaction mixture was cooled and concentrated to dryness to give an oil. The oil was dissolved in dichloromethane and applied to a silica gel coated preparative chromatography plate. The plate was developed with a mixture of 3 parts toluene-2 parts acetonitrile (v/v). The major band was removed, washed with acetone, and the acetone solution was concentrated to dryness to provide 50 mg of diphenylmethyl [2R-2-(3-phenoxymethyl)-7-oxo-4-oxa-2,6-diazabicyclo[3.2.0]hept-2-en-6-yl]-3-hydroxymethyl-3-butenoate.

NMR ($CDCl_3$) δ4.08 (s, 2H); δ4.6 (s, 2H); δ4.98–5.4 (m, 4H); δ5.8 (s, 1H), δ6.7–7.4 (m, 16H).

EXAMPLE 3

The procedure of Example 2 was followed, except that isobutyl alcohol was employed as the reaction solvent. Following purification by chromatography over silica coated plate, there were obtained 40 mg of diphenylmethyl [2R-2-(3-phenoxymethyl)-7-oxo-4-oxa-2,6-diazabicyclo[3.2.0]hept-2-en-6-yl]-3-hydroxymethyl-3-butenoate. The NMR ($CDCl_3$) was consistent for the proposed product, plus about 20% of the lactone.

NMR ($CDCl_3$) δ4.1 (s, 2H); δ4.55 (s, 2H); δ4.9–5.4 (m, 4H); δ5.8 (d, 1H); δ6.8–7.4 (m, 16H).

The product from above was dissolved in 0.4 ml of ethyl acetate to which was added 1λ of boron trifluoride diethyl etherate (50% in diethyl ether w/v). The reaction mixture stood at room temperature for ninety minutes, and then was diluted by addition of 0.1 ml of 5% aqueous sodium bicarbonate, followed by addition of 0.5% aqueous sodium bicarbonate to pH 7.0. The organic layer was separated, diluted with toluene and concentrated to dryness to give 40 mg of a foam identified as diphenylmethyl 7α-phenoxyacetamido-3-exomethylene-1-oxadethiacepham-4-carboxylate.

NMR ($CDCl_3$) δ4.2 (s, 2H); δ4.45 (s, 2H); δ4.8–5.3 (m, 4H); δ6.7–7.4 (m, 17H).

EXAMPLE 4

The procedure of Example 2 was followed, except that 4 ml of isopropyl alcohol was employed as reaction solvent. The reaction mixture was heated at reflux for ninety-four minutes, cooled, and filtered. The filtrate was concentrated to dryness to give an oil, which was dissolved in 5 ml of ethyl acetate and again concentrated to dryness to give, as a yellow viscous oil, diphenylmethyl [2R-2-(3-phenoxymethyl-7-oxo-4-oxa-2,6-diazabicyclo[3.2.0]hept-2-en-6-yl]-3-hydroxymethyl-3-butenoate.

The product thus obtained was dissolved in 2 ml of ethyl acetate to which were added 5λ of boron trifluoride diethyl etherate. The reaction mixture stood at 24° C. for ninety-four minutes, and then was diluted by addition of 0.8 ml of 0.5% aqueous sodium bicarbonate. The pH was next adjusted to 7 by addition of three drops of 5.0% aqueous sodium bicarbonate. The organic layer was separated and concentrated to dryness to provide 200 mg of diphenylmethyl 7α-phenoxyacetamido-3-exomethylene-1-oxadethiacepham-4-carboxylate, identical to the product of Example 1 by thin layer chromatographic analysis.

We claim:

1. A process for preparing a compound of the formula

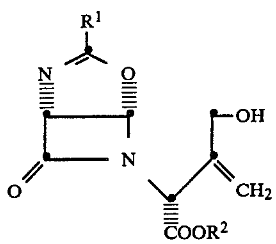

which comprises reacting a triaryl phosphine, trialkyl phosphine, tri(methoxyphenyl)-phosphine, trithienyl-phosphine, tricyanoethyl-phosphine, tricyclohexyl-phosphine, or ethyldicylopropylphosphine with a 3-exomethylene cepham sulfoxide of the formula

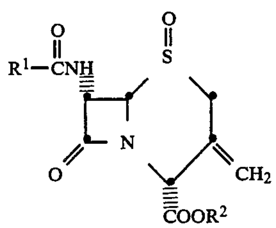

wherein:

$R^1$ is a monovalent residue of a carboxylic acid less the carbonyl group; and $R^2$ is a carboxy protecting group.

2. The process of claim 1 wherein the trisubstituted phosphorus compound is selected from a triaryl phosphine or a trialkylphosphine.

3. The process of claim 2 wherein the trisubstituted phosphorus compound is triphenylphosphine.

4. The process of claim 1 wherein $R^1$ is $C_1$–$C_6$ alkyl, $C_7$–$C_{15}$ arylalkyl, $C_7$–$C_{15}$ heterocyclicalkyl, $C_7$–$C_9$ aryloxyalkyl, $C_7$–$C_9$ heterocyclicoxyalkyl, $C_6$–$C_{10}$ aryl, $C_6$–$C_{10}$ heterocyclic, $C_1$–$C_6$ alkoxy, $C_7$–$C_{15}$ arylalkoxy, $C_7$–$C_{15}$ heterocyclicalkoxy, $C_6$–$C_{10}$ aryloxy, $C_6$–$C_{10}$ heterocyclicoxy, carbamoyl, or $C_2$–$C_7$ carbalkoxy, each of said groups being unsubstituted or substituted by hydroxy, $C_1$–$C_6$ alkanoyloxy, $C_1$–$C_3$ alkoxy, $C_7$–$C_9$ arylalkoxy, $C_6$–$C_8$ aryloxy, oxo, amino, $C_1$–$C_3$ alkylamino, $C_1$–$C_5$ alkanoylamino, nitro, $C_1$–$C_3$ alkyl, $C_6$–$C_{10}$ aryl, carboxy, protected carboxy, cyano or halo.

5. The process of claim 4 wherein $R^2$ is $C_1$–$C_5$ alkyl, $C_7$–$C_{20}$ arylalkyl, $C_6$–$C_{10}$ aryl, or $C_3$–$C_{10}$ organometallic, each of said groups being unsubstituted or substituted by halo, hydroxy, $C_1$–$C_5$ alkanoyloxy, oxo, $C_1$–$C_5$ alkanoylamino, nitro, $C_1$–$C_5$ alkyl, carboxy, $C_2$–$C_6$ carbalkoxy, $C_1$–$C_5$ alkanoyl, or cyano.

6. The process of claim 5 wherein $R^2$ is $C_7$–$C_{20}$ arylalkyl.

7. The process of claim 6 wherein $R^2$ is diphenylmethyl.

8. The process of claim 1 when carried out in an unreactive organic solvent selected from an alcohol or a ketone.

9. The process of claim 8 employing a dialkyl ketone as reaction solvent.

10. The process of claim 1 when carried out at a temperature of about 50° C. to about 100° C.

* * * * *